(12) United States Patent
Chen et al.

(10) Patent No.: US 9,841,375 B2
(45) Date of Patent: Dec. 12, 2017

(54) COHERENTLY RECEIVING SIMULTANEOUS OPTICAL-BASED ELECTRICAL SIGNALS

(71) Applicant: NEWPORT CORPORATION, Irvine, CA (US)

(72) Inventors: Anderson Chen, Stratford, CT (US); John Park, Irvine, CA (US)

(73) Assignee: Newport Corporation, Irvine, CA (US)

( * ) Notice: Subject to any disclaimer, the term of this patent is extended or adjusted under 35 U.S.C. 154(b) by 0 days.

(21) Appl. No.: 15/328,871

(22) PCT Filed: Aug. 1, 2014

(86) PCT No.: PCT/US2014/049489
§ 371 (c)(1),
(2) Date: Jan. 24, 2017

(87) PCT Pub. No.: WO2016/018436
PCT Pub. Date: Feb. 4, 2016

(65) Prior Publication Data
US 2017/0227461 A1    Aug. 10, 2017

(51) Int. Cl.
*G01N 21/00* (2006.01)
*G01N 21/55* (2014.01)
*G01N 21/59* (2006.01)
*G01J 3/02* (2006.01)
(Continued)

(52) U.S. Cl.
CPC ............. *G01N 21/55* (2013.01); *G01N 21/59* (2013.01); *G01J 3/02* (2013.01); *G01N 21/474* (2013.01); *G01N 21/64* (2013.01)

(58) Field of Classification Search
CPC ........ G01N 21/55; G01N 21/59; G01N 21/64; G01N 21/68; G01N 21/474; G01N 21/86; G01N 21/57; G01J 3/02; H01J 37/32
See application file for complete search history.

(56) References Cited

U.S. PATENT DOCUMENTS 6,016,080 A  *  1/2000  Zuta ................. H03L 7/085
                                                  324/76.82
7,619,231 B2    11/2009  Huang
(Continued)

*Primary Examiner* — Abdullahi Nur
(74) *Attorney, Agent, or Firm* — Loza & Loza, LLP; George Fountain

(57) ABSTRACT

Systems for measuring optical properties of a specimen are disclosed. The systems are configured to sample signals related to the measurement of the properties of a specimen, and perform software-based coherent detection of the signals to generate resulting measurements are based on the signals acquired at substantially the same time instance. This facilitates the displaying or generating of the desired measurements in real time. In one configuration, the system is configured to direct a modulated light signal at a selected wavelength incident upon a specimen. In another configuration, the system is configured to direct a combined light signal, derived from a plurality of light signals at different wavelengths and modulated with different frequencies, incident upon a specimen. In yet another configuration, the system is configured to direct a plurality of light signals modulated with different frequencies incident upon different regions of a specimen.

23 Claims, 10 Drawing Sheets

(51) Int. Cl.
    *G01N 21/64*     (2006.01)
    *G01N 21/47*     (2006.01)

(56) References Cited

U.S. PATENT DOCUMENTS

2010/0219327 A1    9/2010    Arbore et al.
2012/0010854 A1    1/2012    Ciocan et al.

* cited by examiner

US 9,841,375 B2

COHERENTLY RECEIVING SIMULTANEOUS OPTICAL-BASED ELECTRICAL SIGNALS

FIELD

This disclosure relates generally to optical systems, and in particular, to a system and method for coherently receiving simultaneous optical-based electrical signals.

BACKGROUND

Optical measurement systems may be used to measure various parameters or characteristics of a specimen (e.g., a device-under-test (DUT) or sample material or component). Generally, an optical measurement system directs incident light at the specimen, and the specimen may produce polarized or unpolarized reflected light, polarized or unpolarized transmitted light, and electrical signal (e.g., current and voltage) in response to the stimulus. The optical measurement system typically includes devices to detect and analyze the reflected light, transmitted light, and/or electrical signal to measure the desired parameters or characteristics of the specimen.

As an example, an optical measurement system for use in measuring the extrinsic quantum efficiency (EQE) of a specimen may include a light source (and other associated components) to generate and direct a defined incident light at the specimen. Such optical measurement system may also include a reference detector to detect a portion of the incident light, and an electrical detector to measure an electrical response (e.g., current or voltage) generated by the specimen in response to the stimuli. Such optical measurement system may include an analysis component to calculate the EQE of the specimen based on signals generated by the measurement system.

Similarly, as another example, an optical measurement system for use in measuring the intrinsic quantum efficiency (IQE) may include a light source (and other associated components) to generate and direct a defined incident light at the specimen. Such optical measurement system may further include a reference detector to detect a portion of the incident light, a specular reflectance detector to detect light reflected at an angle from the specimen, a diffusive reflectance detector to detect scattered light reflected by the specimen, and an electrical detector to detect an electrical response (e.g., current or voltage) generated by the specimen in response to the stimuli. Such optical measurement system may include an analysis component to calculate the IQE of the specimen based on signals generated by the measurement system.

Often, in the aforementioned optical measurement systems, significant noise may be present in the signals measured or generated by the detectors and specimen. In some cases, the noise is so prevalent that DC sampling the signals may not be possible or may result in erroneous detection. To combat noise, some optical measurement systems employ a dedicated lock-in amplifier to extract signals buried in noise. According to this technique, the intensity, frequency, or phase of the incident light is modulated at a frequency. The dedicated lock-in amplifier receives and mixes the detector signal with a signal with an established phase relationship with the modulation frequency (often referred to as coherent or heterodyne detection). The mixed signal is then passed through a filter to generate essentially the detector signal with reduced noise.

A drawback to such optical measurement systems is how task specific the dedicated lock-in amplifier are designed. This makes it difficult to re-configure the system and apply it towards measurements that do not require or cannot utilize lock-in functionality. An example would be in a system that is required to measure both the EQE and IQE of specimens that can or cannot respond to the frequency of modulation on the stimulating light source.

SUMMARY

An aspect of the disclosure relates to a system that may be configured to measure one or more properties of a specimen, such as the extrinsic quantum efficiency (EQE), internal quantum efficiency (IQE), or other properties of the specimen. The system is configured to sample, digitize, and coherently detect signals from the specimen measurement system such that one or more resulting measurements are based on the signals acquired at substantially the same time instance. This facilitates the simultaneous calculation and presentation of the one or more resulting measurements in a real-time manner.

In accordance with a first exemplary embodiment, the system comprises a modulated light source configured to generate a modulated light signal based on a modulation frequency voltage; a specimen measurement system configured to direct at least a portion of the modulated light signal incident upon a specimen for measurement of one or more properties of the specimen, wherein the specimen measurement system is configured to generate a plurality of measurement currents pursuant to the measurement of the one or more properties of the specimen; and a signal conditioner configured to generate a plurality of measurement voltages from the plurality of currents, respectively.

The system also comprises a data acquisition circuit configured to sample and digitize the plurality of measurement voltages to generate a plurality of measurement digital signals, and sample and digitize the modulation frequency voltage to generate a reference digital signal. The sampling of the measurement voltages and modulation frequency voltage is performed in a substantially simultaneous manner. The simultaneous sampling ensures that the one or more resulting measurements, such as EQE and IQE, are based on the currents generated by the specimen measurement system generated at substantially the same time instance. The system comprises a computing device configured to perform software-based coherent detection of the measurement digital signals using the reference digital signal.

In accordance with one embodiment, the computing device may be configured to perform the coherent detection of the measurement digital signals by at least mixing the measurement digital signals with a mixing signal based on the reference digital signal to generate a plurality of respective mixed digital signals, and filtering the digital mixed signals to generate output digital signals. In accordance with another embodiment, the mixing signal may be related to a frequency harmonic of the reference digital signal. Additionally, the computing device may be configured to generate one or more indications of the one or more properties of the specimen based on the output digital signals. Such one or more indications may include the EQE, IQE, or other one or more properties of the specimen.

In accordance with the first embodiment, the specimen measurement system comprises a reference detector configured to generate a first current of the plurality of currents, the first current being related to an intensity of the incident light signal, and wherein a second current of the plurality of currents is generated by the specimen in response to the incident light signal. Alternatively, the specimen measurement system comprises a reference detector configured to generate a first current of the plurality of currents, the first current being related to an intensity of the incident light signal, a reflectance detector configured to generate a second current of the plurality of currents, the second current being related to the intensity of a light signal being reflected by the specimen in response to the incident light signal, and wherein a third current of the plurality of currents is generated by the specimen in response to the incident light signal.

In accordance with a second exemplary embodiment, the system comprises a light source configured to generate a distinct band of wavelength light signals being modulated based on respective distinct modulation frequency voltages; an optical combiner configured to generate a combined light signal based on the distinct band of wavelengths modulated light signals; and a specimen measurement system configured to direct at least a portion of the combined light signal incident upon a specimen for measurement of one or more properties of the specimen, wherein the specimen measurement system is configured to generate a plurality of measurement currents pursuant to the measurement of the one or more properties of the specimen.

In accordance with the second embodiment, the system comprises a signal conditioner configured to generate a plurality of measurement voltages from the plurality of currents, respectively. Further, the system comprises a data acquisition circuit configured to sample and digitize the plurality of measurement voltages to generate a plurality of measurement digital signals, and sample and digitize the plurality of modulation frequency voltages to generate a plurality of reference digital signals. The sampling of the measurement voltages and the modulation frequency voltages are performed in a substantially simultaneous manner. Additionally, the system comprises a computing device configured to perform software-based coherent detection of the measurement digital signals using the reference digital signals.

The computing device may be configured to perform the coherent detection of the measurement digital signals by mixing the measurement digital signals with mixing signals based on the reference digital signals to generate a plurality of mixed digital signals, and filtering the digital mixed signals to generate output digital signals. In one aspect, the mixing signals are related to frequency harmonics of the reference digital signals, respectively. In another aspect, the mixing signals are related to one or more beat frequencies each based on one or more selected pairs of the reference digital signals.

As per the first exemplary embodiment, the computing device is configured to generate one or more indications of the one or more properties of the specimen based on the output digital signals, such as EQE, IQE, or any other one or more properties of the specimen. As per the first exemplary embodiment, the specimen measurement system may be configured to include a reference detector, a reflectance detector, as well as other detectors, and configured to produce the current generated by the specimen in response to the incident light.

In accordance with a third exemplary embodiment, the system comprises a light source configured to generate a plurality of light signals modulated based on a plurality of distinct modulation frequency voltages, respectively; a specimen measurement system configured to direct portions of the plurality of light signals incident upon distinct regions of a specimen for measurement of one or more properties of the specimen, wherein the specimen measurement system is configured to generate a plurality of measurement currents pursuant to the measurement of the one or more properties of the specimen; and a signal conditioner configured to generate a plurality of measurement voltages from the plurality of measurement currents, respectively.

Additionally, in accordance with the third exemplary embodiment, the system comprises a data acquisition circuit configured to sample and digitize the plurality of measurement voltages to generate a plurality of measurement digital signals, and sample and digitize the plurality of modulation frequency voltages to generate a plurality of reference digital signals. The sampling of the measurement voltages and the modulation frequency voltages are performed in a substantially simultaneous manner. In addition, the system comprises a computing device configured to perform software-based coherent detection of the measurement digital signals using the reference digital signals. Other elements of the third embodiment may be configured substantially the same or similar to the second embodiment.

Other aspects, advantages and novel features of the disclosure will become apparent from the following detailed description of the invention when considered in conjunction with the accompanying drawings.

DETAILED DESCRIPTION OF THE EXEMPLARY EMBODIMENTS

Figure 1A:
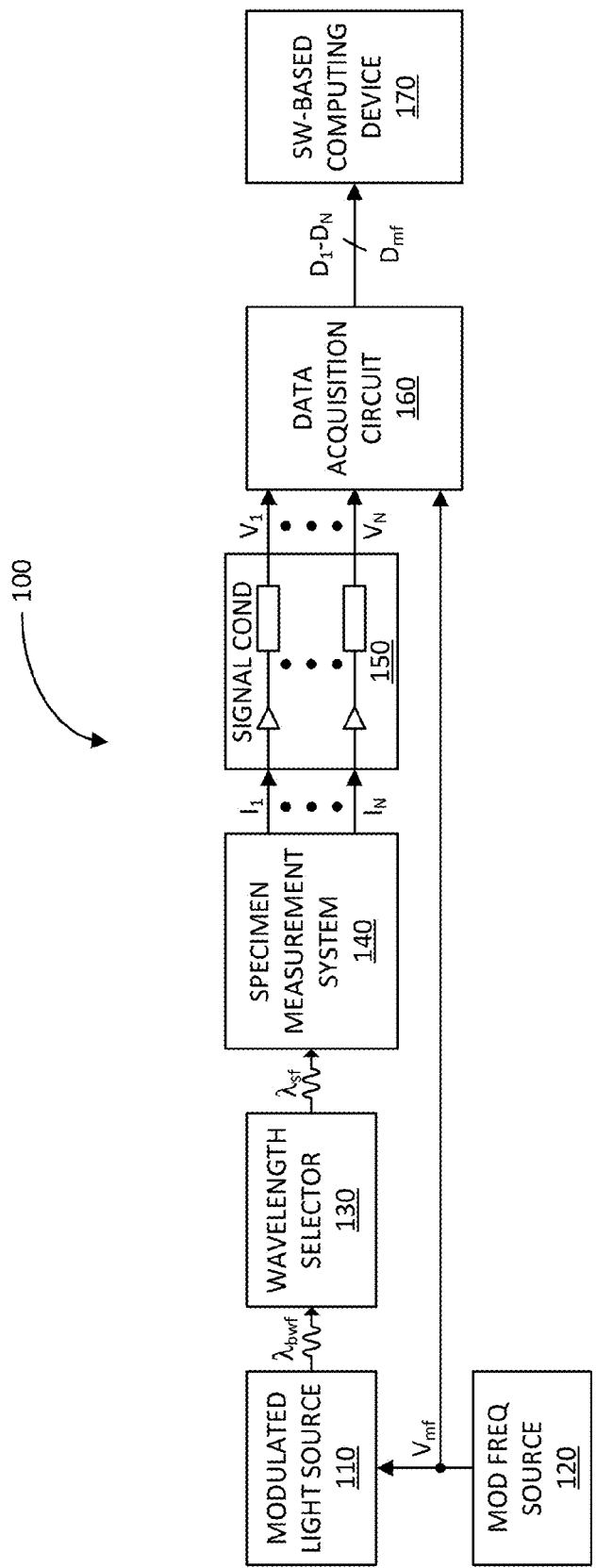
FIG. 1A illustrates a block diagram of an exemplary optical signal processing system in accordance with an aspect of the disclosure.

FIG. 1A illustrates a block diagram of an exemplary optical signal processing system 100 in accordance with an aspect of the disclosure. In summary, the optical signal processing system 100 comprises: a light source configured to generate an incident light at a selected wavelength and amplitude modulated at a particular frequency; a specimen measurement system configured to direct the incident light at a specimen and generate a plurality of signals for measuring one or more characteristics of the specimen; a signal conditioner to generate suitable voltages for acquisition based on the signals generated by the specimen measurement system; a data acquisition circuit to substantially perform simultaneous sampling and digitizing of the voltages from the signal conditioner; and a software-based (SW-based) computing device configured to perform coherent detection and analysis of the digitized signals.

The simultaneous sampling and coherent detection of the signals allow the SW-based computing device to more accurately generate one or more measurements of the specimen in real-time. This is because the one or more measurements depend on a plurality of signals generated at substantially the same time. In other words, inaccuracy or noise due to time differences in the acquisition of the signals is minimized. Additionally, because a plurality of measurements depend on different sets of signals generated from the specimen measurement system, the simultaneous sampling and coherent detection ensures that different measurements are based on signals acquired at substantially the same time. Further, such different measurements may be accurately displayed simultaneously in real-time.

More specifically, the optical signal processing system 100 comprises a modulated light source 110, a modulation frequency source 120, a wavelength selector 130, a specimen measurement system 140, a signal conditioning circuit 150, a data acquisition circuit 160, and a SW-based computing device 170.

The modulated light source 110 generates a modulated light with a defined range or bandwidth (bw) of wavelengths $\lambda_{bwf}$. Examples of modulated light source may include lasers, diodes, and other types of light sources. The modulated light source 110 generates the modulated light $\lambda_{bwf}$ based on a modulation signal or voltage $V_{mf}$, which cycles with a defined frequency (f). The modulation frequency source 120 generates the modulation signal or voltage $V_{mf}$ for the modulated light source 110. The wavelength selector 130 generates a modulated light with a selected wavelength $\lambda_{sd}$ from the modulated light $\lambda_{bwf}$, wherein the selected wavelength $\lambda_{sf}$ has a narrower band than the modulated light $\lambda_{bwf}$. The wavelength selector 130 may comprise a monochromator, filter, or other device capable of selecting a more narrowband wavelength within the wavelength range of the modulated light $\lambda_{bwf}$.

The specimen measurement system 140 is configured to direct the selected modulated light $\lambda_{sf}$ incident upon a specimen for measurement of one or more properties or characteristics of the specimen. In accordance with the measurement, the specimen measurement system 140 generates a plurality of electrical signals, such as currents $I_1$ to $I_N$.

For example, if the specimen measurement system 140 is configured to measure the extrinsic quantum efficiency (EQE) of a specimen, the specimen measurement system 140 may generate a current $I_1$ related to the power level of the incident light $\lambda_{sf}$ upon the specimen, and a current $I_2$ generated by the specimen in response to the incident light $\lambda_{sf}$. If the specimen measurement system 140 is configured to measure the intrinsic quantum efficiency (IQE) of a specimen, the specimen measurement system 140 may generate a current $I_1$ related to the power level of the incident light $\lambda_{sf}$ upon the specimen, a current $I_2$ related to a power level of specular light reflected by the specimen, a current $I_3$ related to a power level of diffusive light reflected by the specimen, and a current $I_4$ generated by the specimen in response to the incident light $\lambda_{sf}$. It shall be understood that the specimen measurement system 140 may be configured to measure both EQE and IQE, as well as perform other measurements on the specimen.

The signal conditioning circuit 150 performs transimpedance amplification and signal conditioning of the currents $I_1$ to $I_N$ to generate voltages $V_1$ to $V_N$ suitable for sampling and digitizing by the data acquisition circuit 160. For example, the signal conditioning circuit 150 may perform the transimpedance amplification with a positive gain to generate the voltages $V_1$ to $V_N$ at suitable levels, and apply filtering and/or other processing to reduce noise.

As previously discussed the data acquisition circuit 160 samples and digitizes the voltages $V_1$ to $V_N$ from the signal conditioning circuit 150 to generate digital signals $D_1$ to $D_N$, respectively. Additionally, the data acquisition circuit 160 samples and digitizes the modulation voltage $V_{mf}$ from the modulation frequency source 120 to generate digital signal $D_{mf}$. So that the coherent detection and any measurements performed by the SW-based computing device are based on the currents $I_1$ to $I_N$ derived at substantially the same time, the data acquisition circuit 160 is configured to simultaneously sample the voltages $V_1$ to $V_N$ and the modulation voltage $V_{mf}$.

The SW-based computing device 170 receives the digital signals $D_1$ to $D_N$ and $D_{mf}$ by way of any suitable digital interface, such as a Universal Serial Bus (USB) interface, Peripheral Component Interface (PCI), and others. The SW-based computing device may be any type of computing device, such as a desktop computer, laptop, smart phone, tablet-type computer, and others. As discussed in more detail herein, the SW-based computing device 170 performs software-based coherent detection (also known as heterodyne or lock-in amplifier detection) to generate, potentially less-noisy, digital output signals related to the intensity or power level of the currents $I_1$ to $I_N$ generated at substantially the same time instance. The SW-based computing device 170 performs the coherent detection of the digital signals $D_1$ to $D_5$ in a manner that the resulting output signals are derived from the currents $I_1$ to $I_5$ at substantially the same time instance. This ensures time correlation for all the variables needed for the SW-based computing device 370 to derive the resulting one or more measurements (e.g., EQE and IQE) of the specimen.

Additionally, the SW-based computing device 170 may output the resulting one or more measurements, as well as the data derived from the specimen measurement system 140 and other associated data, to a user interface, such as a display, speakers, etc., to provide a user information related to the one or more measurements. Via the user interface, as in the case of input devices such as a keyboard, mouse, microphones, etc., the SW-based computing device 170 may receive instructions from a user as to how to perform the one or more measurements and how the information is provided to the user via the user interface. In this regards, the SW-based computing device 170 may send control signals to any of the elements of the system 100 to configure the system in accordance with the user's inputs.

Figure 1B:
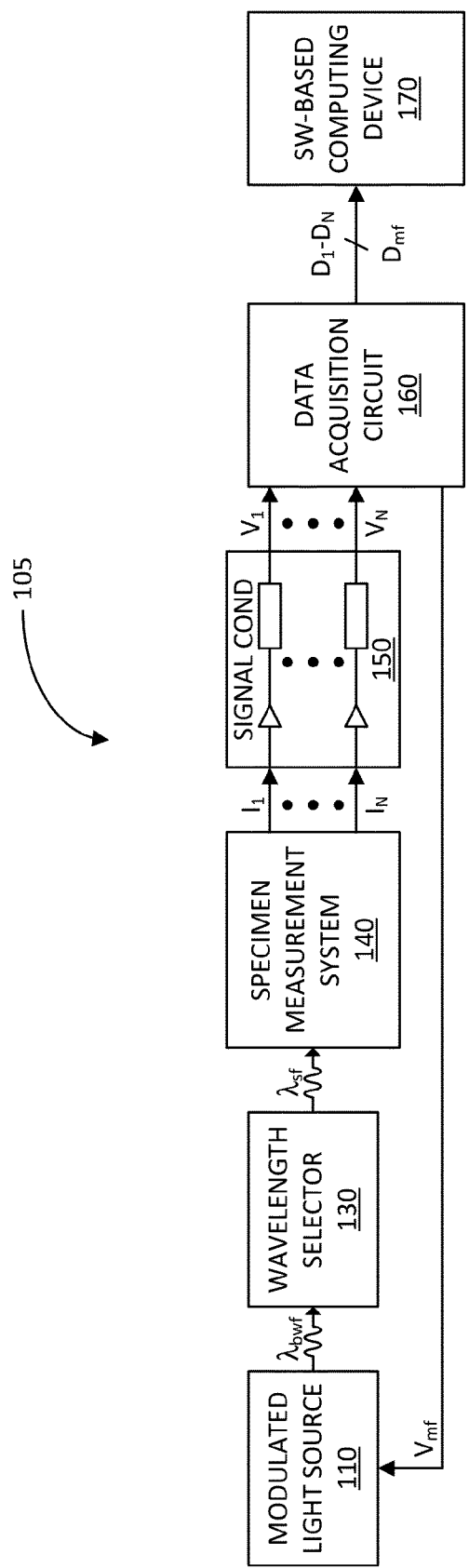
FIG. 1B illustrates a block diagram of yet another exemplary optical signal processing system in accordance with another aspect of the disclosure.

FIG. 1B illustrates a block diagram of yet another exemplary optical signal processing system 105 in accordance with another aspect of the disclosure. The optical signal processing system 105 is a variation of the optical signal processing system 100 previously discussed, and includes many of the same elements as noted by the same reference numbers. The system 105 differs from system 100 in that the modulation signal or voltage $V_{mf}$ is generated internally within the data acquisition circuit 160, and not by an external modulation frequency source 120 as in system 100. Otherwise, the operation of the optical signal processing system 105 is substantially the same as optical signal processing system 100 previously discussed in detail.

Figure 1C:
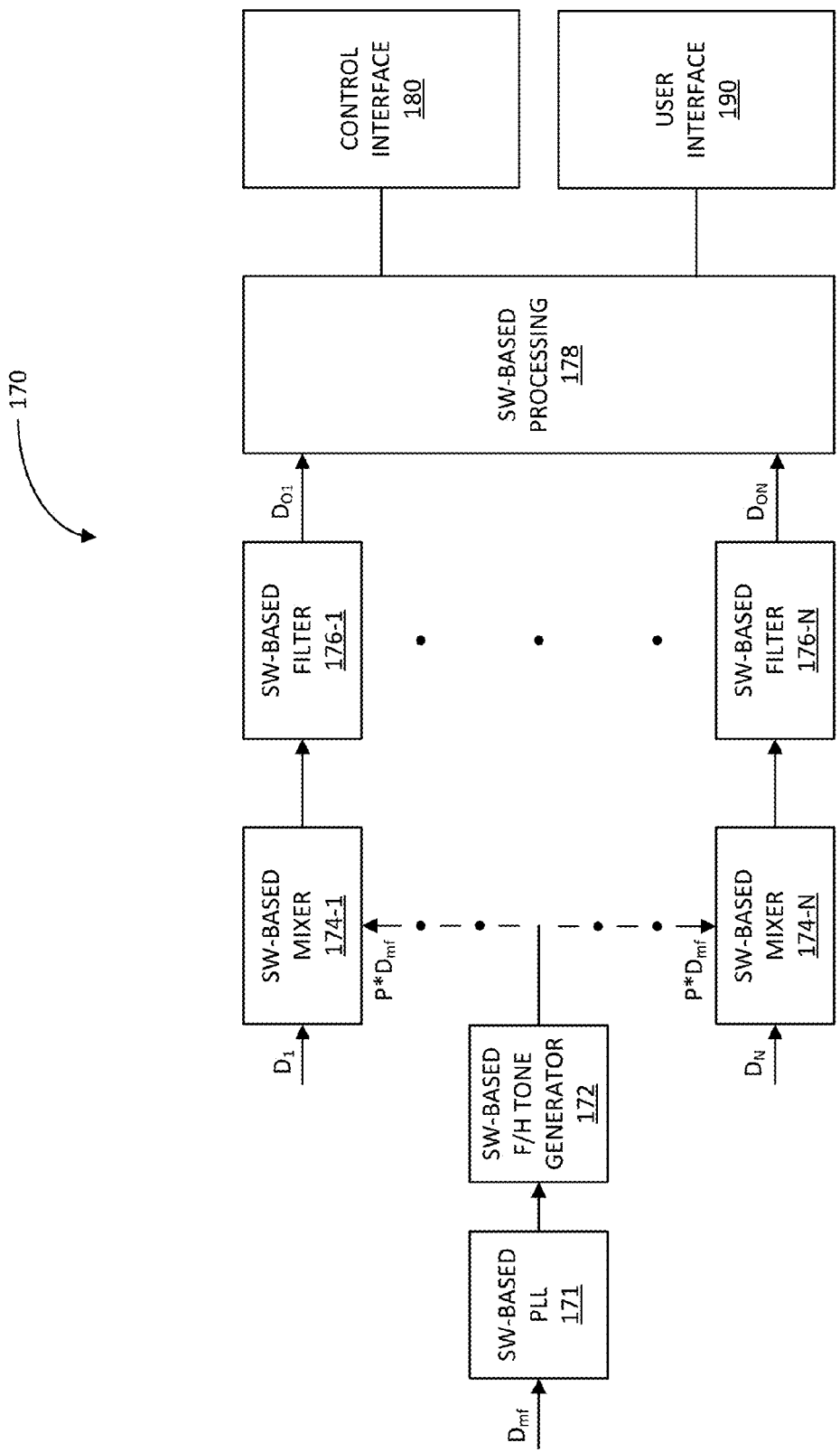
FIG. 1C illustrates a block diagram of an exemplary software-based coherent detection system in accordance with another aspect of the disclosure.

FIG. 1C illustrates a block diagram of an exemplary software-based coherent detection system implemented by the exemplary SW-based computing device 170 in accordance with another aspect of the disclosure. The system 170 comprises a SW-based phase lock loop (PLL) module 171, a SW-based frequency/harmonic (F/H) tone generator module 172, SW-based mixer modules 174-1 to 174-N, SW-based filter modules 176-1 to 176-N, and a SW-based processing module 178. The SW-based processing module 178 may interface with a control interface 180 for sending and/or receiving signals, such as control signals and sensed parameters, to and from other elements of the optical signal processing system 100 or 105. Additionally, the SW-based processing module 178 may interface with a user interface 190 for sending and/or receiving signals, such as measurement-related information and control signals, to and from a user of the optical signal processing system 100 or 105.

The SW-based PLL module 171 is configured to generate a signal that is phase locked with the digital signal $D_{mf}$. Since the digital signal $D_{mf}$ is derived from the modulation signal $V_{mf}$, the signal generated by the SW-based PLL module 171 is phase locked with the modulation signal $V_{mf}$. Based on a selected fundamental or harmonic command P, the SW-based F/H tone generator 172 may regenerate the fundamental signal $D_{mf}$ in the case P is equal to one (1), or may generate a desired harmonic $P*D_{mf}$ of the signal in the case P is an integer greater than one (1). The harmonic may be used to detect harmonic components of the modulation frequency in the digital signals $D_1$ to $D_N$. Although not shown for simplicity sake, the output signal $P*D_{mf}$ of the SW-based F/H tone generator 172 includes both the sine and cosine components for proper heterodyne detection at the SW-based mixer modules 174-1 to 174-N.

As mentioned, the selected tone $P*D_{mf}$ from the SW-based F/H tone generator 172 is applied to the SW-based mixer modules 174-1 to 174-N. The digital signals $D_1$ to $D_N$ are also applied to the SW-based mixer modules 174-1 to 174-N, respectively. The SW-based mixer modules 174-1 to 174-N mixes the digital signals $D_1$ to $D_N$ with the selected tone $P*D_{mf}$ to generate respective mixed signals. Each of the mixed signals includes a direct current (DC) carrier component and a sideband component. The sideband component may be associated with noise in the system 100 or 105. The corresponding SW-based filters 176-1 to 176-N substantially eliminate the sideband components of the mixed signals to generate output signals $D_{O1}$ to $D_{ON}$, respectively. The output signals $D_{O1}$ to $D_{ON}$ are related to the power level or intensity of the signals or currents $I_1$ to $I_N$ generated by the specimen measurement system 140.

The SW-based processing module 178 processes the output signals $D_{O1}$ to $D_{ON}$ in accordance with the one or more desired measurements of one or more characteristics of the specimen. For example, if the optical signal processing system 100 or 105 is configured to measure EQE and/or IQE, the SW-based processing system 178 generates parameters indicative of the EQE and/or IQE based on the output signals $D_{O1}$ to $D_{ON}$. The SW-based processing module 178 may send the measurement information to the user interface 190 to provide a user such information, in a graphical or non-graphical manner.

Figure 2A:
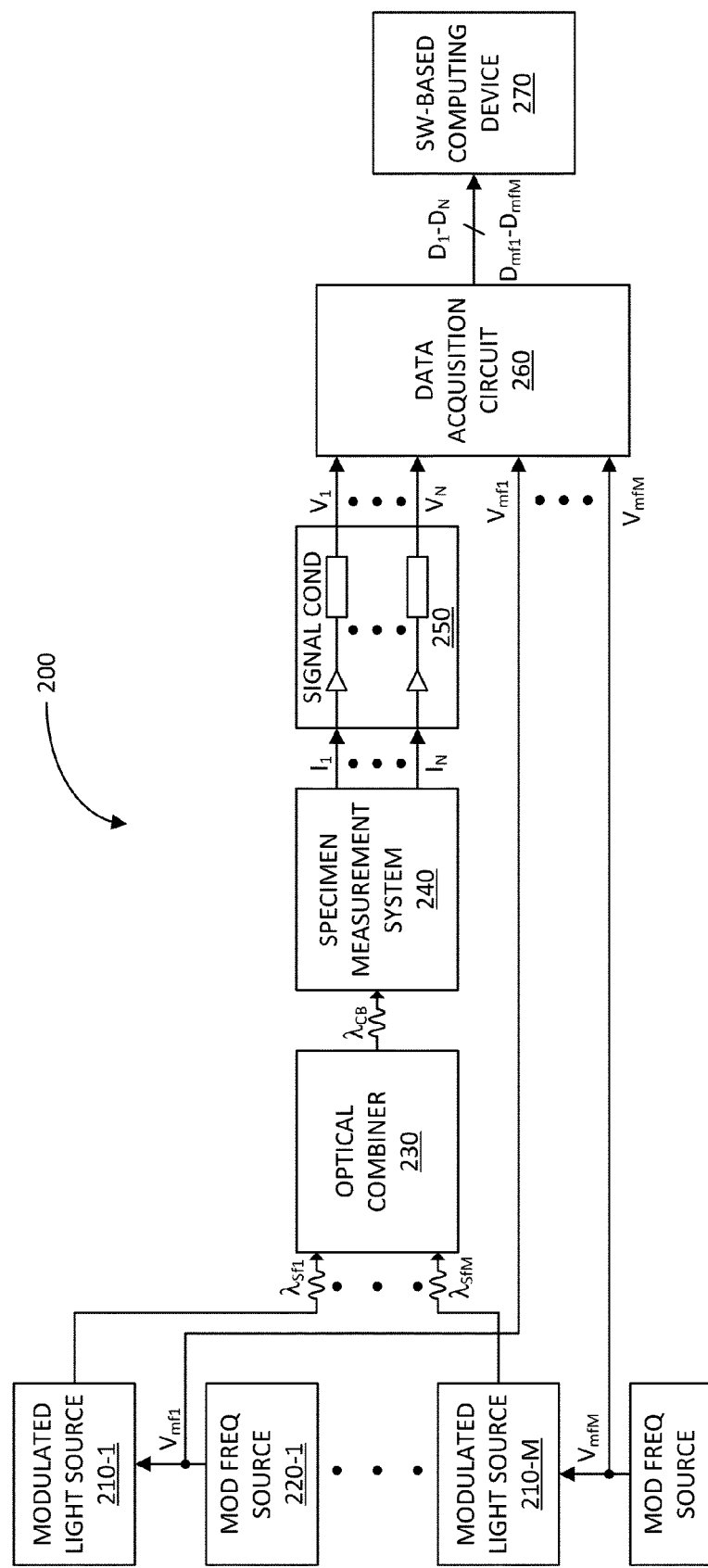
FIG. 2A illustrates a block diagram of another exemplary optical signal processing system in accordance with an aspect of the disclosure.

FIG. 2A illustrates a block diagram of another exemplary optical signal processing system 200 in accordance with another aspect of the disclosure. In the previous exemplary embodiments, the systems 100 and 105 were configured to generate an incident light for the specimen, whereby the incident light is configured with a selected wavelength and modulated at a particular frequency. In contrast, the optical signal processing system 200 is configured to generate a combined incident light for the specimen, whereby the combined incident light is derived from a plurality of lights at different wavelengths and modulated with different frequencies.

More specifically, the optical signal processing system 200 comprises modulated light sources 210-1 to 210-M, modulation frequency sources 220-1 to 220-M, an optical combiner 230, a specimen measurement system 240, signal conditioning circuit 250, a data acquisition circuit 260, and a SW-based computing device 270.

The modulated light sources 210-1 to 210-M generate lights $\lambda_{sf1}$ to $\lambda_{sfM}$ configured with different wavelengths and modulated at different frequencies, respectively. The modulated light sources 210-1 to 210-M generate $\lambda_{sf1}$ to $\lambda_{sfM}$ based on modulation signals or voltages $V_{mf1}$ to $V_{mfM}$ generated by the modulation frequency sources 220-1 to 220-M, respectively. Alternatively, instead of the external modulation frequency sources 220-1 to 220-M, the modulation signals or voltages $V_{mf1}$ to $V_{mfM}$ may be generated internally in the data acquisition circuit 260, as per optical signal processing system 105.

The optical combiner 230 receive the respective lights $\lambda_{sf1}$ to $\lambda_{sfM}$ from the modulated light sources 210-1 to 210-M, and combines them to generate a combined light $\lambda_{cb}$. As an example, the optical combiner 230 may be configured as a homogenizing rod/coupler or other type of optical signal combining device. The combined light $\lambda_{cb}$ is provided to the specimen measurement system 240, which directs it incident upon a specimen. As per the previous specimen measurement system 140, the specimen measurement system 240 generates a plurality of electrical signals $I_1$ to $I_N$ associated with the one or more measurements being performed on the specimen. Similar to the previous embodiments, the specimen measurement system 240 may be configured to generate electrical signals $I_1$ to $I_N$ pursuant to an EQE and/or IQE measurement.

Similar to the previous embodiments, the signal conditioning circuit 250 performs transimpedance amplification of the currents $I_1$ to $I_N$ and associated signal conditioning to generate corresponding voltages $V_1$ to $V_N$ suitable for sampling and digitizing by the data acquisition circuit 260.

The data acquisition circuit 260 samples and digitizes the voltages $V_1$ to $V_N$ from the signal conditioning circuit 250 to generate digital signals $D_1$ to $D_N$. The data acquisition circuit 260 also samples the modulation voltages $V_{mf1}$ to $V_{mfM}$ from the modulation frequency sources 220-1 to 220-N to generate digital signals $D_{mf1}$ to $D_{mfM}$, respectively. As per the previous embodiments, the data acquisition circuit 260 simultaneously samples and digitizes the voltages $V_1$ to $V_N$ and $V_{mf1}$ to $V_{mfM}$ so that the resulting measurement(s) generated by the SW-based computing device 270 are based on signals derived from the specimen at substantially the same time instance.

As per the previous embodiments, the SW-based computing device 270 receives the digital signals $D_1$ to $D_N$ and $D_{mf1}$ to $D_{mfM}$ via a digital interface (e.g., USB, PCI, etc). The SW-based computing device 270 performs coherent detection of the digital signals $D_1$ to $D_N$ using the modulation-based signals $D_{mf1}$ to $D_{mfM}$ to generate output digital signals indicative of the intensity or power level of the currents $I_1$ to $I_N$ from the specimen measurement system 240. The SW-based computing device 270 performs the coherent detection of the digital signals $D_1$ to $D_5$ in a manner that the resulting output signals are derived from the currents $I_1$ to $I_5$ at substantially the same time instance. This ensures time correlation for all the variables needed for the SW-based computing device 270 to derive the resulting one or more measurements (e.g., EQE and IQE) of the specimen.

Figure 2B:
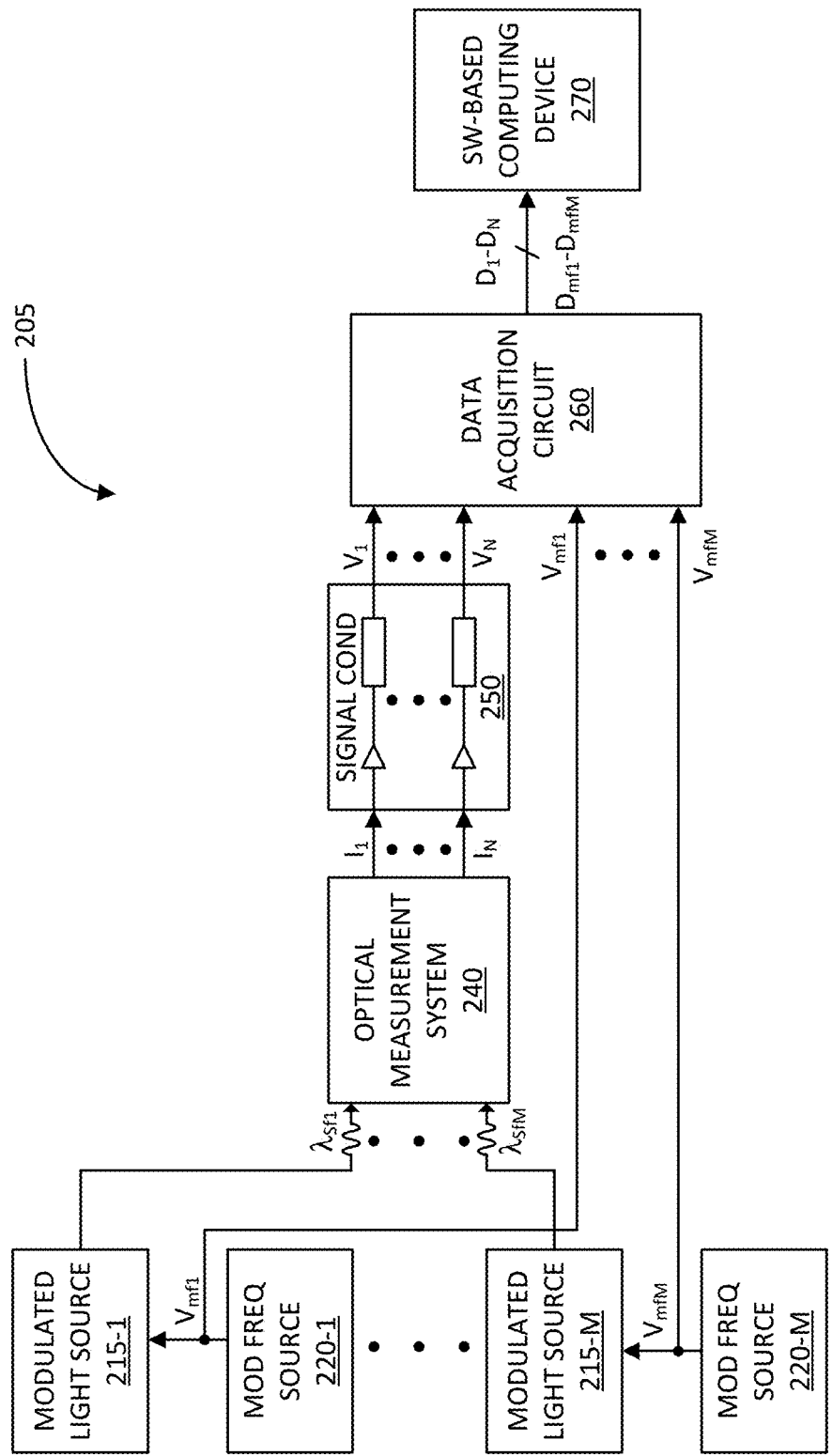
FIG. 2B illustrates a block diagram of yet another exemplary optical signal processing system in accordance with another aspect of the disclosure.

FIG. 2B illustrates a block diagram of yet another exemplary optical signal processing system 205 in accordance with another aspect of the disclosure. The optical signal processing system 205 is a variation of the optical signal processing system 200, and includes many of the same elements as indicated by the same reference numbers. The optical signal processing system 205 differs from optical signal processing system 200 in that the modulated light sources 215-1 to 215-M may generate light signals $\lambda_{sf1}$ to $\lambda_{sfM}$ with substantially the same wavelength, but modulated with different frequencies.

Another difference is that the light signals $\lambda_{sf1}$ to $\lambda_{sfM}$ are transmitted separately into the specimen measurement system 240. The specimen measurement system 240 directs the light signals $\lambda_{sf1}$ to $\lambda_{sfM}$ at different regions of a specimen. This may be done to perform spatial analysis of the specimen. The resulting currents $I_1$ to $I_N$ generated by the specimen measurement system 240 may each have contributions from the light signals $\lambda_{sf1}$ to $\lambda_{sfM}$. Using coherent detection, the SW-based computing device 270 is capable of separating the contributions for individual analysis thereof.

Figure 2C:
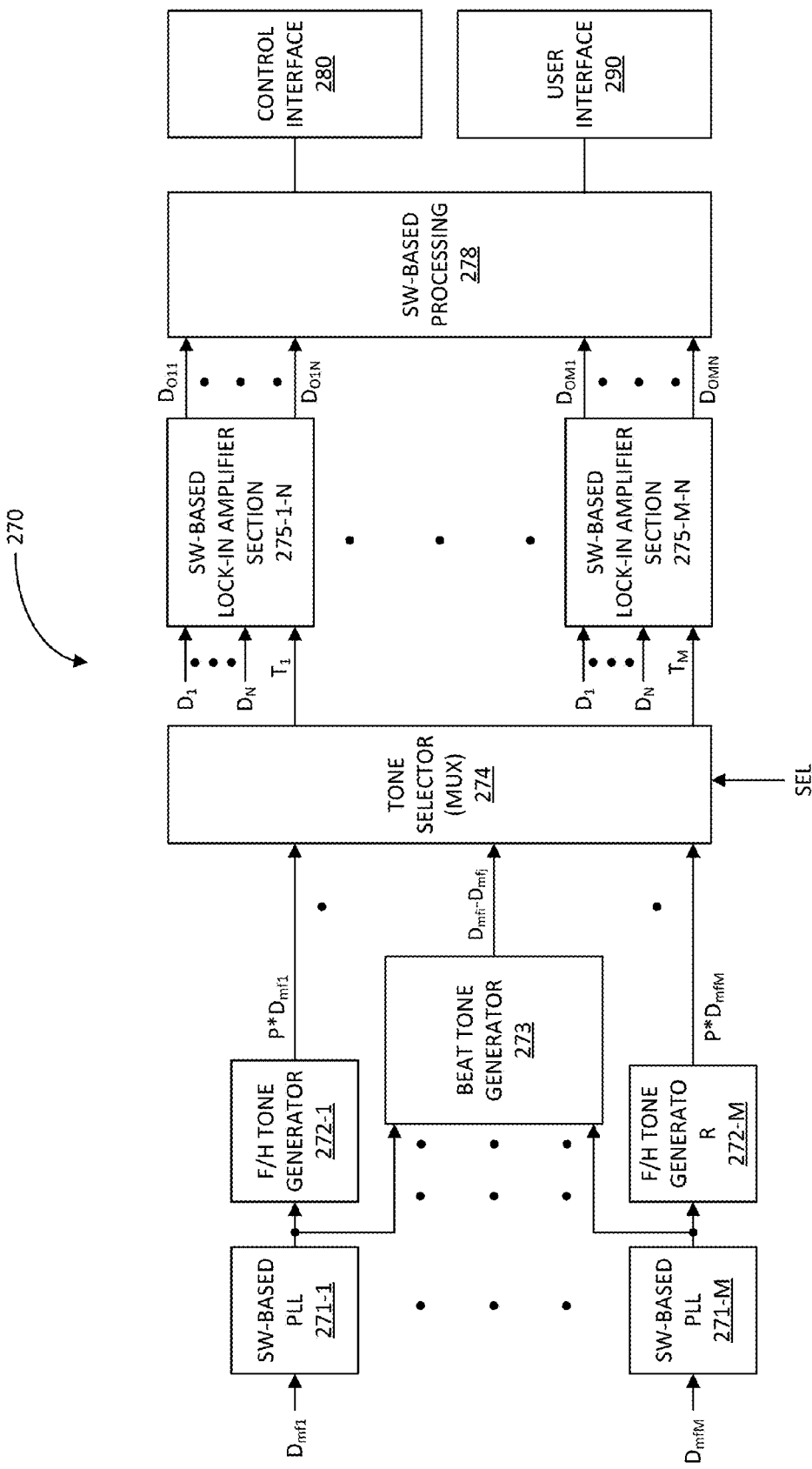
FIG. 2C illustrates a block diagram of another exemplary software-based coherent detection system in accordance with another aspect of the disclosure.

FIG. 2C illustrates a block diagram of another exemplary software-based coherent detection system implemented by the exemplary SW-based computing device 270 in accordance with another aspect of the disclosure. The SW-based computing device 270 comprises a plurality of SW-based PLL modules 272-1 to 271-M, a plurality of F/H tone generator modules 272-1 to 272-M, and a beat tone generator module 273. Additionally, the SW-based computing device 270 further comprises a tone selector (mux) 274, a plurality of SW-based coherent or lock-in amplifier sections 275-1-N to 275-M-N, and a SW-based processing module 278. As per the previous embodiments, the SW based processing module 278 may interface with a control interface 280 for sending control signals and receiving sensed parameters, and may also interface with a user interface 290 for providing and receiving information to and from a user.

The SW-based PLL modules 271-1 to 271-M generate signals phase locked with the digital signals $D_{mf1}$ to $D_{mfM}$, respectively. The F/H tone generator modules 272-1 to 272-M generate fundamental (P=1) or harmonics (P>1) signals $P^*D_{mf1}$ to $P^*D_{mfM}$ based on user selected parameter P, respectively. The beat tone generator module 273 generates a selected beat frequency signal $D_{mfi}-D_{mfj}$ based on a selected pair i and j of the phase locked signals generated from the SW-based PLL modules 271-1 to 271-M. The generated signals or tones $P^*D_{mf1}$ to $P^*D_{mfM}$ and $D_{mfi}-D_{mfj}$ are provided to the tone selector module 274. Based on a user select signal (SEL), the tone selector module 274 outputs selected tones $T_1$ to $T_M$.

The SW-based coherent or lock-in amplifier sections 275-1-N to 275-M-N use the selected tones T1 to TM to generate coherently-detected output signals $D_{O11}$ to $D_{OMN}$, respectively. For instance, if the fundamental frequencies $D_{mf1}$ to $D_{mfM}$ are chosen for the selected tones $T_1$ to $T_M$, then the output signals $D_{O11}-D_{O1N}$ to $D_{OM1}-D_{OMN}$ indicate the intensity or power level of the fundamental frequency components of the current signals $I_1$ to $I_N$ from the specimen measurement system 240, respectively. If harmonic frequencies $P^*D_{mf1}$ to $P^*D_{mfM}$ (P>1) are chosen for the selected tones $T_1$ to $T_M$, then the output signals $D_{O11}-D_{O1M}$ to $D_{OM1}-D_{OMN}$ indicate the intensity or power level of the selected harmonic frequency components of the current signals $I_1$ to $I_N$ from the specimen measurement system 240, respectively. Similarly, if a certain beat frequency is chosen for the selected tones $T_1$ to $T_M$, then the output signals $D_{O11}-D_{O1N}$ to $D_{OM1}-D_{OMN}$ indicate the intensity or power level of the selected beat frequency component of the current signals $I_1$ to $I_N$ from the specimen measurement system 240, respectively.

The SW-based processing module 278 processes the output signals $D_{O11}-D_{O1N}$ to $D_{OM1}-D_{OMN}$ in accordance with the one or more desired measurements of one or more characteristics of the specimen. For example, if the optical signal processing system 200 or 205 is configured to measure EQE and/or IQE, the SW-based processing system 278 generates parameters indicative of the EQE and/or IQE based on the output signals $D_{O11}-D_{O1N}$ to $D_{OM1}-D_{OMN}$. The SW-based processing module 278 may send the measurement information to the user interface 290 to provide a user such information, in a graphical or non-graphical manner.

Figure 3:
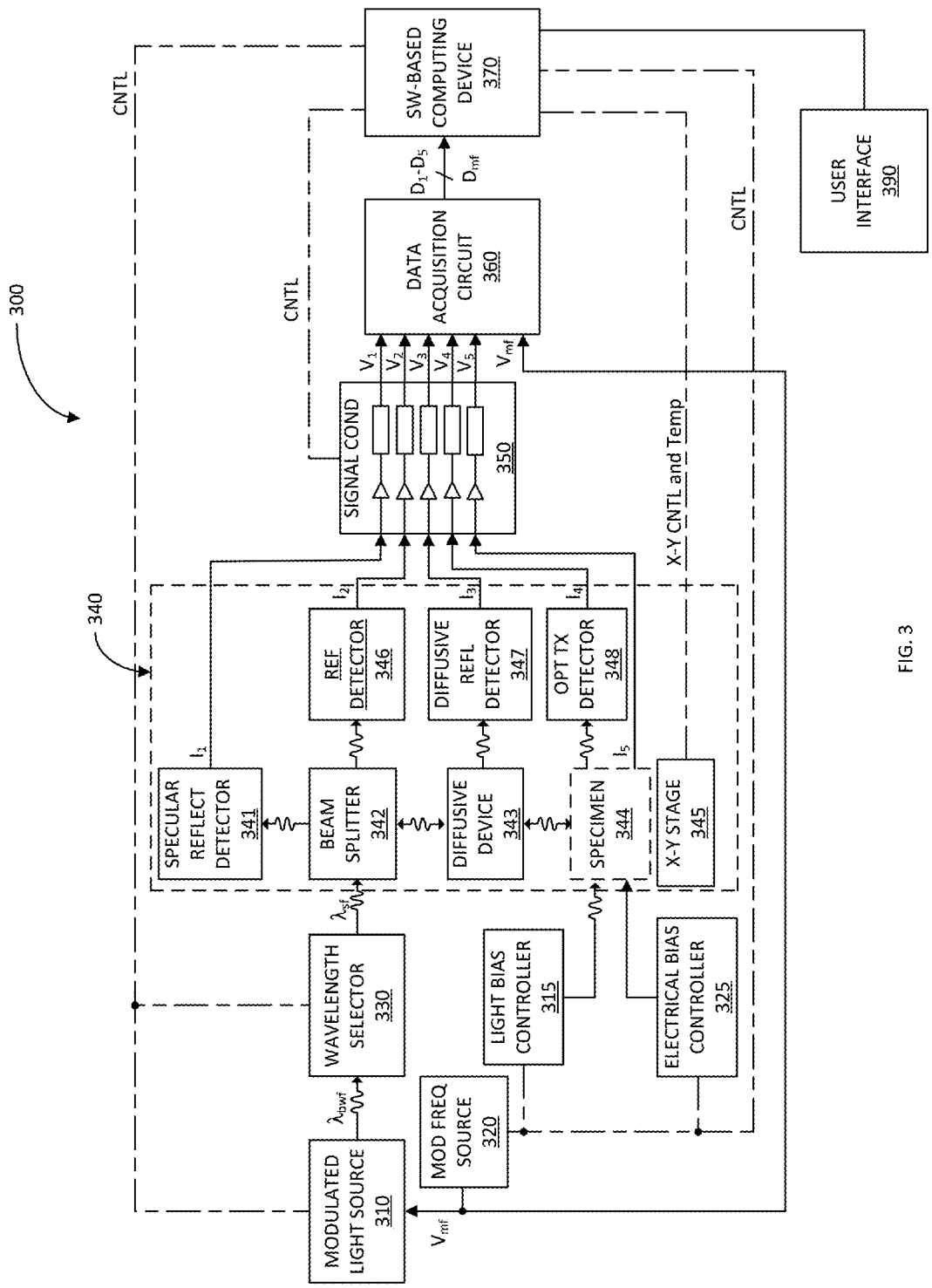
FIG. 3 illustrates a block diagram of another exemplary optical signal processing system in accordance with another aspect of the disclosure.

FIG. 3 illustrates a block diagram of another exemplary optical signal processing system 300 in accordance with another aspect of the disclosure. The optical signal processing system 300 is an exemplary implementation of optical signal processing system 100 previously discussed, with a specimen measurement system being configured to measure EQE and/or IQE.

In particular, the optical signal processing system 300 comprises a modulated light source 310, a modulation frequency source 320, a wavelength selector 330, a light bias controller 315, an electrical bias controller 325, a specimen measurement system 340, a signal conditioning circuit 350, a data acquisition circuit 360, a SW-based computing device 370, and a user interface 390. The specimen measurement system 340, in turn, comprises a specular reflectance detector 341, a beam splitter 342, a diffusive device 343, a specimen 344, an X-Y stage 345, a reference detector 346, a diffusive reflectance detector 347, and an optical transmission detector 348.

The modulated light source 310 is configured to generate a modulated light signal having a defined range of wavelengths $\lambda_{bwf}$. The modulated light source 310 is configured to generate the light signal $\lambda_{bwf}$ based on a modulation signal or voltage $V_{mf}$ generated by the modulation frequency source 320. The wavelength selector 330 is configured to generate a modulated light signal having a selected wavelength $\lambda_{sf}$ based on the light signal $\lambda_{bwf}$ from the modulated light source 310, wherein the selected wavelength $\lambda_{sf}$ has a narrower band than the modulated light $\lambda_{bwf}$. As previously discussed with reference to system 100, the wavelength selector 330 may comprise a monochromator, filter or other devices.

With regard to the specimen measurement system 340, the beam splitter 342 splits the light signal $\lambda_{sf}$ into a reference signal and an incident signal. The reference signal is provided to the reference detector 346. In response to the reference signal, the reference detector 346 generates a current $I_2$. The current $I_2$ is related (e.g., proportional) to the intensity or power level of the light source $\lambda_{sf}$. The incident signal is directed to the specimen 344 by way of the diffusive device 343. The diffusive device 343 may comprises an integration sphere or other type of diffusive device.

The specimen 344 may generate a current $I_5$ in response to the diffusive incident light. The current $I_5$ may be used to determine the EQE and IQE, as well as other properties of the specimen 344. In some cases, some of the incident light may pass or transmit through the specimen 344, which may be detected by optical transmission detector 348. In response to the transmitted light, the optical transmission detector 348 generates a current $I_4$. The current $I_4$ may be used to determine the EQE and IQE, as well as other properties of the specimen 344.

Some of the incident light is reflected off of the specimen 344. The reflected light is received by the diffusive device 343. The diffusive device 343 includes a port for outputting the diffusive reflected light. A diffusive reflectance detector 347 generates a current $I_3$ in response to the diffusive reflected light from the diffusive device 343. The current $I_3$ may be used to determine the EQE and IQE, as well as other properties of the specimen 344. Additionally, some of the incident light reflected off of the specimen 344 at a normal angle, referred to herein as specular reflected light, passes through the diffusive device 343 and the beam splitter 343, and is detected by the specular reflectance detector 341. The specular reflectance detector 341 generates a current $I_1$ in response to the specular reflected light. The current $I_1$ may be used to determine the EQE and IQE, as well as other properties of the specimen 344.

The X-Y stage 345 of the specimen measurement system 340 supports the specimen 344, and facilitates the positioning of the specimen 344 either manually by a user or by way of an X-Y control signal generated by the SW-based computing device 370. The X-Y stage 345 may further include a sensor for generating a signal indicative of the temperature of the specimen. The X-Y stage 345 may provide the temperature signal to the SW-based computing device 370 via a control line.

The light bias controller 315 of the optical signal processing system 300 may direct a controllable light at the specimen 344 in accordance with one or more measurements being made with regard to the specimen. In this regards, the SW-based computing device 370 generates a control signal for the light bias controller 315. Additionally, the electrical bias controller 325 may bias the specimen 344 with a controllable bias signal (e.g., a bias voltage and/or current) in accordance with one or more measurements being made with regard to the specimen. In this regards, the SW-based computing device 370 generates a control signal for the electrical bias controller 325.

As per the previous embodiments, the signal conditioning circuit 350 receives the currents $I_1$ to $I_5$ from the specimen measurement system 340 and generates therefrom respective voltages $V_1$ to $V_5$ suitable for sampling and digitizing by the data acquisition circuit 360. As per the previous embodiments, the data acquisition circuit 360 samples and digitizes the voltages $V_1$ to $V_5$ and the modulation frequency voltage $V_{mf}$ to generate digital signals $D_1$ to $D_5$ and $D_{mf}$, respectively. As per the previous embodiment, the data acquisition circuit 360 samples these voltages in a substantially simultaneous manner.

The SW-based computing device 370 performs the coherent detection of the digital signals $D_1$ to $D_5$ in a manner that the resulting output signals are derived from the currents $I_1$ to $I_5$ at substantially the same time instance. This ensures time correlation for all the variables needed for the SW-based computing device 370 to derive the EQE and IQE, as well as other properties of the specimen. As per the previous embodiments, the SW-based computing device 370 may provide and receive control-related signals to and from various elements of the optical signal processing system 300 per control lines indicated as alternate long-and-short-dashes. Additionally, the SW-based computing device 370 may provide and receive measurement-related information to and from a user via the user interface 390.

Figure 4:
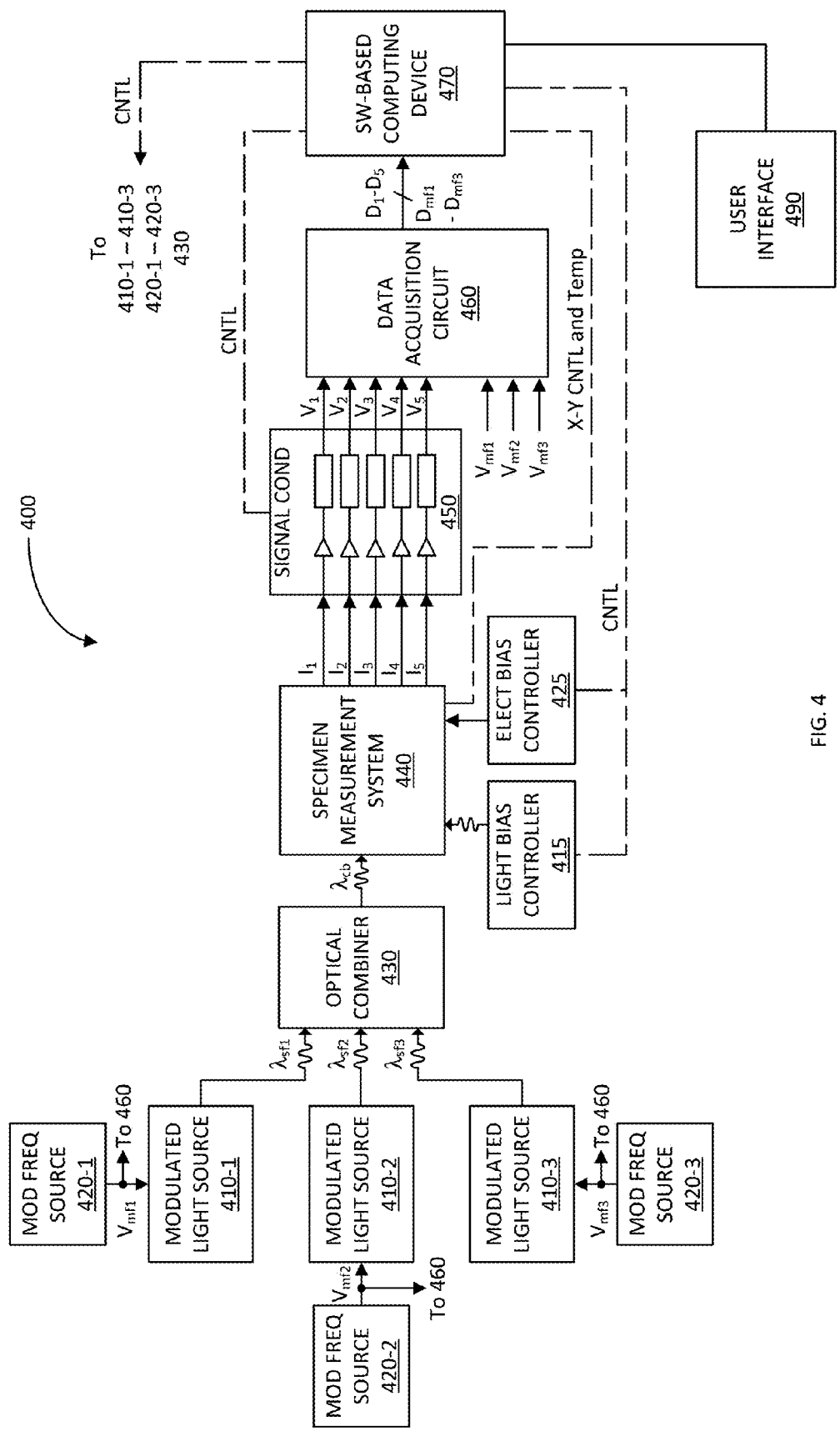
FIG. 4 illustrates a block diagram of yet another exemplary optical signal processing system in accordance with another aspect of the disclosure.

FIG. 4 illustrates a block diagram of yet another exemplary optical signal processing system 400 in accordance with another aspect of the disclosure. The optical signal processing system 400 is an exemplary implementation of optical signal processing system 200 previously discussed, with a specimen measurement system being configured to measure EQE and/or IQE.

In particular, the optical signal processing system 400 comprises modulated light sources 410-1 to 410-3, modulation frequency sources 420-1 to 420-3, an optical combiner 430, a light bias controller 415, an electrical bias controller 425, a specimen measurement system 440, a signal conditioning circuit 450, a data acquisition circuit 460, a SW-based computing device 470, and a user interface 490.

Modulated light sources 420-1 to 420-3 are configured to generate modulated light signals having distinct selected wavelengths $\lambda_{sf1}$, $\lambda_{sf2}$, and $\lambda_{sf3}$, and modulated with distinct frequencies based on modulation signals or voltages $V_{mf1}$, $V_{mf2}$ and $V_{mf3}$ generated by the modulation frequency sources 420-1, 420-2, and 420-3, respectively. The optical combiner 430 combines the modulated light signals $\lambda_{sf1}$, $\lambda_{sf2}$, and $\lambda_{sf3}$ to generate a combined light signal $\lambda_{cb}$. The specimen measurement system 440 uses the combined light signal $\lambda_{cb}$ to generate an incident light for a specimen. The specimen measurement system 440 may be configured substantially the same or similar to specimen measurement system 340, previously discussed in detail.

As per the previous embodiment, the specimen measurement system 440 generates currents $I_1$ to $I_5$. The signal conditioner 450 performs transimpedance amplification and signal conditioning to convert the currents $I_1$ to $I_5$ into suitable voltages $V_1$ to $V_5$ for sampling and digitizing by the data acquisition circuit 460. As per the previous embodiments, the data acquisition circuit 460 samples and digitizes the voltages $V_1$ to $V_5$ and the modulation voltages $V_{mf1}$ to $V_{mf3}$ to generate digital signals $D_1$ to $D_5$ and $D_{mf1}$ to $D_{mf3}$, respectively. The data acquisition circuit 460 samples and digitizes the signals in a substantially simultaneous manner.

As per SW-based computing device 270 previously discussed, the SW-based computing device 470 performs coherent detection of the digital signals $D_1$ to $D_5$ using modulation signals $D_{mf1}$ to $D_{mf3}$ to generate output digital signals. If, for example, the coherent detection uses the fundamental tones $D_{mf1}$ to $D_{mf3}$, the detected output signals indicate the intensity or power level of the fundamental frequency component of the currents $I_1$ to $I_5$ generated by the specimen measurement system 440. If, for example, the coherent detection uses harmonics $P^*D_{mf1}$ to $P^*D_{mf3}$ (P>1), the detected output signals indicate the intensity or power level of the corresponding harmonic frequency component of the currents $I_1$ to $I_5$ generated by the specimen measurement system 440. If, for example, the coherent detection uses a selected beat frequency $(D_{mfi} \pm D_{mfj})(i \neq j, i=j=\{1,2,3\})$, the detected output signals indicate the intensity or power level of the corresponding beat frequency component of the currents $I_1$ to $I_5$ generated by the specimen measurement system 440.

The SW-based computing device 470 performs the coherent detection of the digital signals $D_1$ to $D_5$ in a manner that the resulting output signals are derived from the currents $I_1$ to $I_5$ at substantially the same time instance. This ensures time correlation for all the variables needed for the SW-based computing device 470 to derive the EQE and IQE, as well as other properties of the specimen. As per the previous embodiments, the SW-based computing device 470 may provide and receive control-related signals to and from various elements of the optical signal processing system 400 per control lines indicated as alternate long-and-short-dashes. Additionally, the SW-based computing device 470 may provide and receive measurement-related information to and from a user via the user interface 490.

As per the previous embodiment, the light bias controller 415 of the optical signal processing system 400 directs controllable light at the specimen in accordance with one or more measurements being made with regard to the specimen. In this regards, the SW-based computing device 470 generates a control signal for the light bias controller 415. The electrical bias controller 425 biases the specimen with a controllable bias signal (e.g., a bias voltage and/or current) in accordance with one or more measurements being made with regard to the specimen. In this regards, the SW-based computing device 470 generates a control signal for the electrical bias controller 425.

Figure 5:
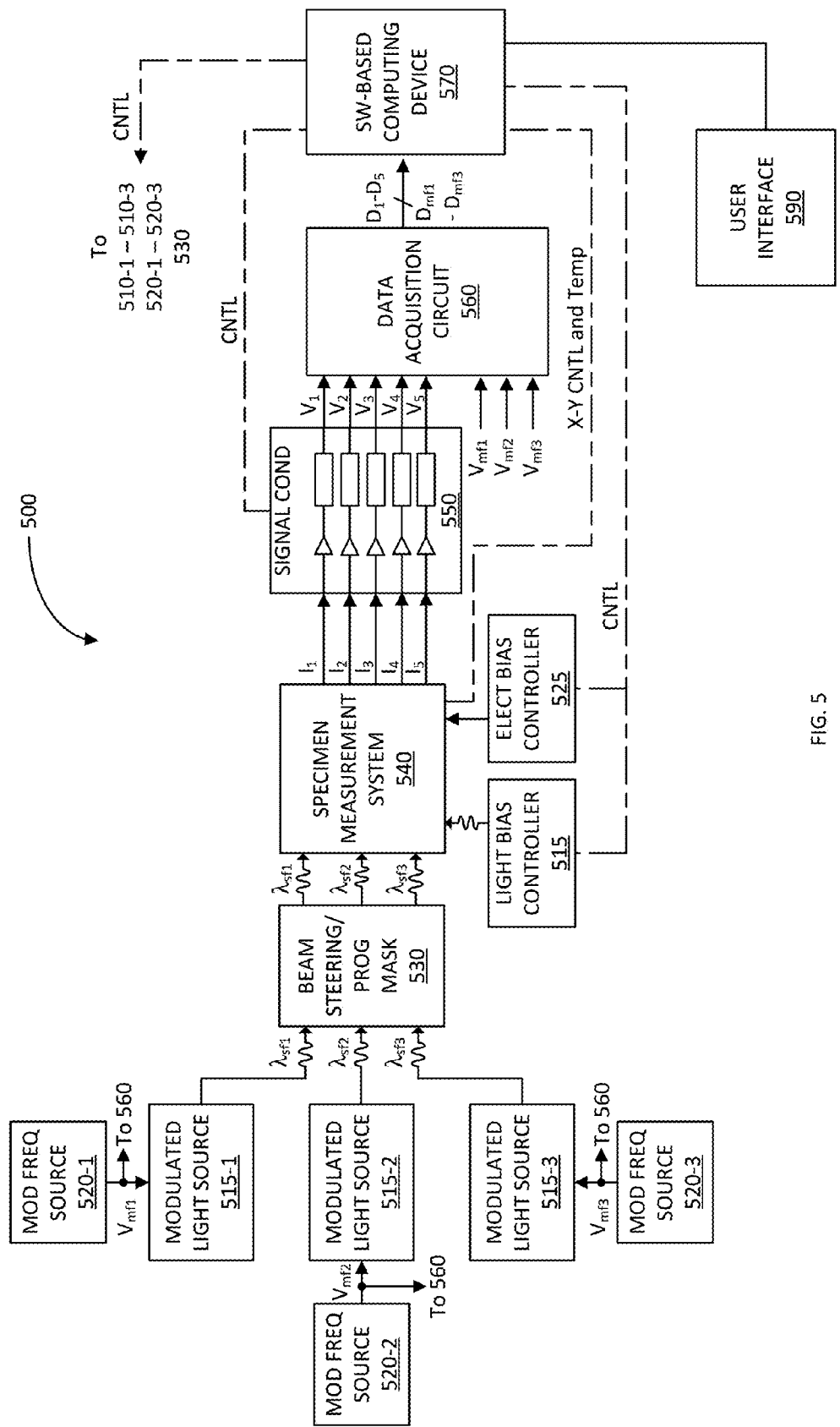
FIG. 5 illustrates a block diagram of still another exemplary optical signal processing system in accordance with another aspect of the disclosure.

FIG. 5 illustrates a block diagram of still another exemplary optical signal processing system 500 in accordance with another aspect of the disclosure. The optical signal processing system 500 is an exemplary implementation of the optical signal processing system 205 previously discussed, with a specimen measurement system being configured to measure EQE and/or IQE.

In particular, the optical signal processing system 500 comprises modulated light sources 510-1 to 510-3, modulation frequency sources 520-1 to 520-3, beam steering or programmable mask 530, a light bias controller 515, an electrical bias controller 525, a specimen measurement system 540, a signal conditioning circuit 550, a data acquisition circuit 560, a SW-based computing device 570, and a user interface 590.

Modulated light sources 520-1 to 520-3 are configured to generate modulated light signals $\lambda_{sf1}$, $\lambda_{sf2}$, and $\lambda_{sf3}$ having substantially the same wavelength, but modulated with distinct frequencies based on modulation signals or voltages $V_{mf1}$, $V_{mf2}$ and $V_{mf3}$ generated by the modulation frequency sources 520-1, 520-2, and 520-3, respectively. The beam steering/programmable mask 530 is configured to direct the modulated light signals $\lambda_{sf1}$, $\lambda_{sf2}$, and $\lambda_{sf3}$ to desired regions of a specimen. The specimen measurement system 540 uses the modulated light signals $\lambda_{sf1}$, $\lambda_{sf2}$, and $\lambda_{sf3}$ to generate incident light signals for a specimen for spatial analysis thereof. The specimen measurement system 540 may be configured substantially the same or similar to specimen measurement system 340, previously discussed in detail.

As per the previous embodiments, the specimen measurement system 540 generates currents $I_1$ to $I_5$. The signal conditioning circuit 550 performs transimpedance amplification and signal conditioning to convert the currents $I_1$ to $I_5$ into suitable voltages $V_1$ to $V_5$ for sampling and digitizing by the data acquisition circuit 560. As per the previous embodiments, the data acquisition circuit 560 samples and digitizes the voltages $V_1$ to $V_5$ and the modulation voltages $V_{mf1}$ to $V_{mf3}$ to generate digital signals $D_1$ to $D_5$ and $D_{mf1}$ to $D_{mf3}$, respectively. The data acquisition circuit 560 samples the signals in a substantially simultaneous manner.

As per SW-based computing device 270 previously discussed, the SW-based computing device 570 performs coherent detection of the digital signals $D_1$ to $D_5$ using modulation signals $D_{mf1}$ to $D_{mf3}$ to generate detected output signals. If, for example, the coherent detection uses the fundamental tones $D_{mf1}$ to $D_{mf3}$, the detected output signals indicate the intensity or power level of the fundamental frequency component of the currents $I_1$ to $I_5$ generated by the specimen measurement system 540. If, for example, the coherent detection uses harmonics $P*D_{mf1}$ to $P*D_{mf3}$ (P>1), the detected output signals indicate the intensity or power level of the corresponding harmonic frequency component of the currents $I_1$ to $I_5$ generated by the specimen measurement system 540. If, for example, the coherent detection uses a selected beat frequency $(D_{mfi} \pm D_{mfj})(i \neq j, i=j=\{1,2,3\})$, the detected output signals indicate the intensity or power level of the corresponding beat frequency component of the currents $I_1$ to $I_5$ generated by the specimen measurement system 540.

The SW-based computing device 570 performs the coherent detection of the digital signals $D_1$ to $D_5$ in a manner that the resulting output signals are derived from the currents $I_1$ to $I_5$ at substantially the same time instance. This ensures time correlation for all the variables needed for the SW-based computing device 570 to derive the EQE and IQE, as well as other properties of the specimen. As per the previous embodiments, the SW-based computing device 570 may provide and receive control-related signals to and from various elements of the optical measurement system 500 per control lines indicated as alternate long-and-short-dashes. Additionally, the SW-based computing device 570 may provide and receive measurement-related information to and from a user via the user interface 590.

As per the previous embodiment, the light bias controller 515 of the optical measurement system 500 directs controllable light at the specimen in accordance with one or more measurement being made with regard to the specimen. The SW-based computing device 570 generates a control signal for the light bias controller 515. The electrical bias controller 425 biases the specimen with a controllable bias signal (e.g., a bias voltage and/or current) in accordance with one or more measurement being made with regard to the specimen. In this regards, the SW-based computing device 570 generates a control signal for the electrical bias controller 525.

Figure 6:
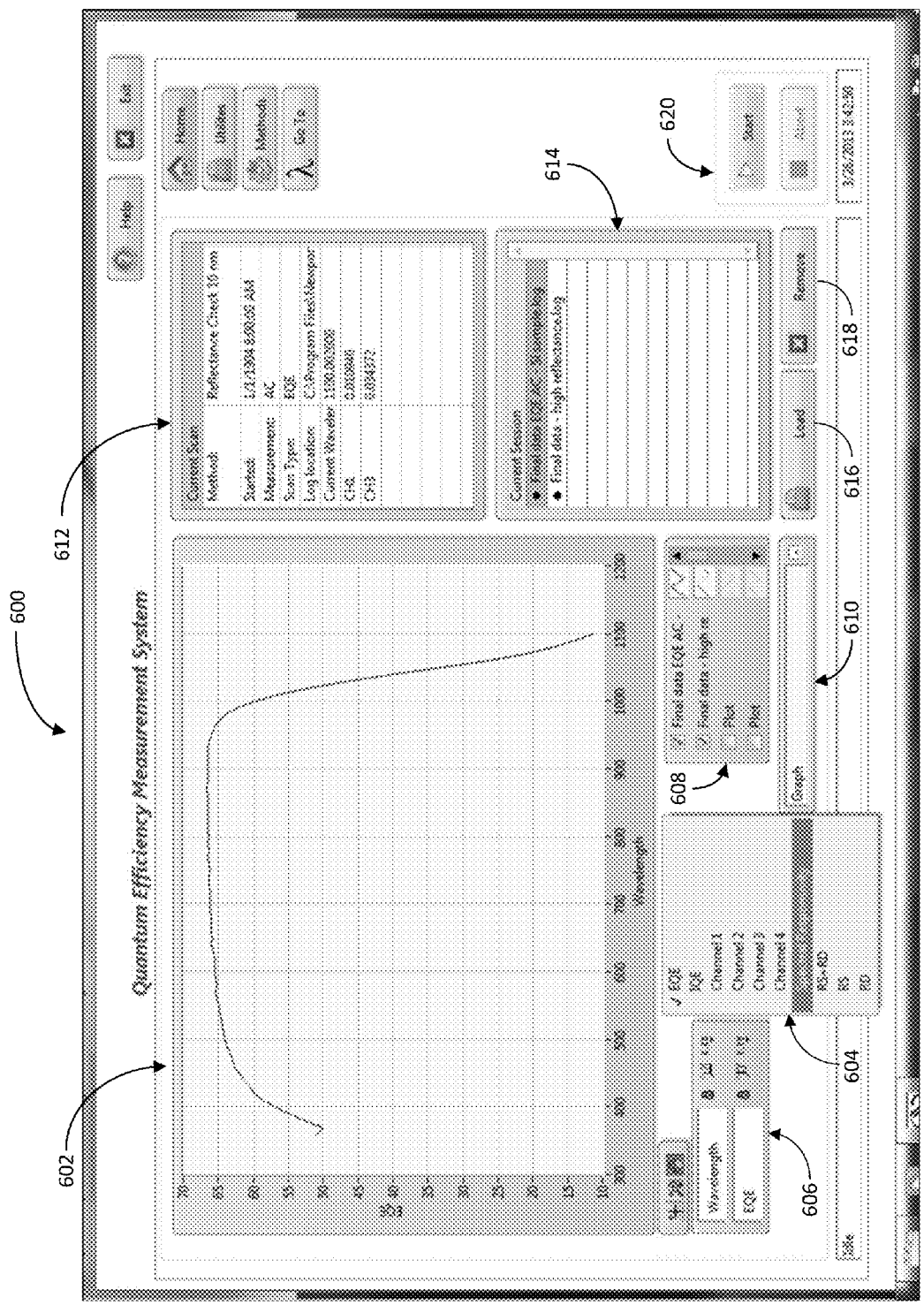
FIG. 6 illustrates a screen shot of an exemplary graphical user interface (GUI) generated by an exemplary user interface in accordance with another aspect of the disclosure.

FIG. 6 illustrates a screen shot of an exemplary graphical user interface (GUI) 600 generated by an exemplary user interface in accordance with another aspect of the disclosure. The GUI 600 comprises a measurement display portion 602 configured to illustrate one or more selected measurements. In this example, the measurement display portion 602 depicts a graph of the EQE measurement in graph form. The x- or horizontal-axis represents wavelength, and the y- or vertical axis represents EQE. It shall be understood that the measurement display portion 602 may illustrate the one or more selected measurements in other formats, such as tabulated, pie charts, bar charts, and others. For instance, the display portion 602 may display the EQE, IQE, RS, and RD at the same time during a wavelength scan.

The GUI 600 further comprises a measurement selection portion 604 configured to allow a user to select one or more measurements for depiction in the measurement display portion 602. For instance, in this example, the measurement selection portion 604 illustrates the EQE as being the selected measurement, as indicated by the juxtaposed checkmark. Additionally, in accordance with this example, the measurement selection portion 604 lists other available measurements, such as IQE, channels 1-4 (e.g., related to the various signals generated by a specimen measurement system described herein), spectral responsivity, signal from specular reflectance detector (RS), signal from diffusive reflectance detector (RS), and sum of signals from specular and diffusive reflectance detectors (RS+RD). It shall be understood that more or less different types of measurements may be available to a user via the measurement selection portion 604.

The GUI 600 further comprises a graph labeling portion 606 with text boxes for allowing a user to label the x- and y-axes of the graph depicted in the measurement display portion 602. Additionally, the GUI 600 comprises a legend area 608 for identifying the plot. This is useful when the graph depicts multiple plots. Also, the GUI 600 includes a drop-down box 610 to allow a user to select the display format for the one or more selected measurements, such as graph, tabulated, and others.

The GUI 600 also comprises a scan detail area 612 that provides information related to the current scan. The GUI 600 also includes a current session 614 indicating the data log files related to the current session. Using the load and remove soft buttons 616 and 618, a user is able to load the data from a selected data log file, as well as remove a data log file. Further, the GUI 600 includes start and abort soft buttons 620 to allow a user to start a measurement scan and to abort a measurement scan. It shall be understood that GUI 600 is merely an example, and the GUI may be configured in many different manners.

While the invention has been described in connection with various embodiments, it will be understood that the invention is capable of further modifications. This application is intended to cover any variations, uses or adaptation of the invention following, in general, the principles of the invention, and including such departures from the present disclosure as come within the known and customary practice within the art to which the invention pertains.

What is claimed is:

1. A system, comprising:
   a modulated light source configured to generate a modulated light signal based on a modulation frequency voltage;
   a specimen measurement system configured to direct at least a portion of the modulated light signal incident upon a specimen for measurement of one or more properties of the specimen, wherein the specimen measurement system is configured to generate a plurality of measurement currents pursuant to the measurement of the one or more properties of the specimen;
   a signal conditioner configured to generate a plurality of measurement voltages from the plurality of currents, respectively;
   a data acquisition circuit configured to:
      sample and digitize the plurality of measurement voltages to generate a plurality of measurement digital signals; and
      sample and digitize the modulation frequency voltage to generate a reference digital signal, wherein the sampling of the measurement voltages and modulation frequency voltage are performed in a substantially simultaneous manner; and
   a computing device configured to perform software-based coherent detection of the measurement digital signals using the reference digital signal.

2. The system of claim 1, wherein the computing device is configured to perform the coherent detection of the measurement digital signals by at least:
   mixing the measurement digital signals with a mixing signal based on the reference digital signal to generate a plurality of mixed digital signals, respectively; and
   filtering the digital mixed signals to generate output digital signals.

3. The system of claim 2, wherein the mixing signal is related to a frequency harmonic of the reference digital signal.

4. The system of claim 2, wherein the computing device is configured to generate one or more indications of the one or more properties of the specimen based on the output digital signals.

5. The system of claim 4, wherein the one or more indications includes an extrinsic quantum efficiency (EQE), intrinsic quantum efficiency (IQE), or both the EQE and IQE of the specimen.

6. The system of claim 1, wherein the specimen measurement system comprises:
   a reference detector configured to generate a first current of the plurality of currents, the first current being related to an intensity of the incident light signal; and
   wherein a second current of the plurality of currents is generated by the specimen in response to the incident light signal.

7. The system of claim 1, wherein the specimen measurement system comprises:
   a reference detector configured to generate a first current of the plurality of currents, the first current being related to an intensity of the incident light signal;
   a reflectance detector configured to generate a second current of the plurality of currents, the second current being related to an intensity of a light signal reflected by the specimen in response to the incident light signal; and
   wherein a third current of the plurality of currents is generated by the specimen in response to the incident light signal.

8. A system, comprising:
   a light source configured to generate a plurality of distinct wavelengths light signals modulated based on a plurality of distinct modulation frequency voltages, respectively;
   an optical combiner configured to generate a combined light signal based on the plurality of distinct wavelengths light signals;
   a specimen measurement system configured to direct at least a portion of the combined light signal incident upon a specimen for measurement of one or more properties of the specimen, wherein the specimen measurement system is configured to generate a plurality of measurement currents pursuant to the measurement of the one or more properties of the specimen;
   a signal conditioner configured to generate a plurality of measurement voltages from the plurality of currents, respectively;
   a data acquisition circuit configured to:
      sample and digitize the plurality of measurement voltages to generate a plurality of measurement digital signals; and
      sample and digitize the plurality of modulation frequency voltages to generate a plurality of reference digital signals, wherein the sampling of the measurement voltages and the modulation frequency voltages are performed in a substantially simultaneous manner; and
   a computing device configured to perform software-based coherent detection of the measurement digital signals using the reference digital signals.

9. The system of claim 8, wherein the computing device is configured to perform the coherent detection of the measurement digital signals by at least:
   mixing the measurement digital signals with mixing signals based on the reference digital signals to generate a plurality of mixed digital signals, respectively; and filtering the digital mixed signals to generate output digital signals.

10. The system of claim 9, wherein the mixing signals are related to frequency harmonics of the reference digital signals, respectively.

11. The system of claim 9, wherein the mixing signals are related to one or more beat frequencies each based on at least a pair of the reference digital signals.

12. The system of claim 9, wherein the computing device is configured to generate one or more indications of the one or more properties of the specimen based on the output digital signals.

13. The system of claim 12, wherein the one or more indications include an extrinsic quantum efficiency (EQE), intrinsic quantum efficiency (IQE), or both the EQE and IQE of the specimen.

14. The system of claim 8, wherein the specimen measurement system comprises:
a reference detector configured to generate a first current of the plurality of currents, the first current being related to an intensity of the incident light signal; and
wherein a second current of the plurality of currents is generated by the specimen in response to the incident light signal.

15. The system of claim 8, wherein the specimen measurement system comprises:
a reference detector configured to generate a first current of the plurality of currents, the first current being related to an intensity of the incident light signal;
a reflectance detector configured to generate a second current of the plurality of currents, the second current being related to an intensity of a light signal reflected by the specimen in response to the incident light signal; and
wherein a third current of the plurality of currents is generated by the specimen in response to the incident light signal.

16. A system, comprising:
a light source configured to generate a plurality of light signals modulated based on a plurality of distinct modulation frequency voltages, respectively;
a specimen measurement system configured to direct portions of the plurality of light signals incident upon distinct regions of a specimen for measurement of one or more properties of the specimen, wherein the specimen measurement system is configured to generate a plurality of measurement currents pursuant to the measurement of the one or more properties of the specimen;
a signal conditioner configured to generate a plurality of measurement voltages from the plurality of currents, respectively;
a data acquisition circuit configured to:
sample and digitize the plurality of measurement voltages to generate a plurality of measurement digital signals; and
sample and digitize the plurality of modulation frequency voltages to generate a plurality of reference digital signals, wherein the sampling of the measurement voltages and the modulation frequency voltages are performed in a substantially simultaneous manner; and
a computing device configured to perform software-based coherent detection of the measurement digital signals using the reference digital signals.

17. The system of claim 16, wherein the computing device is configured to perform the coherent detection of the measurement digital signals by at least:
mixing the measurement digital signals with mixing signals based on the reference digital signals to generate a plurality of mixed digital signals, respectively; and
filtering the digital mixed signals to generate output digital signals.

18. The system of claim 17, wherein the mixing signals are related to frequency harmonics of the reference digital signals, respectively.

19. The system of claim 17, wherein the mixing signals are related to one or more beat frequencies each based on at least a pair of the reference digital signals.

20. The system of claim 17, wherein the computing device is configured to generate one or more indications of the one or more properties of the specimen based on the output digital signals.

21. The system of claim 20, wherein the one or more indications include an extrinsic quantum efficiency (EQE), intrinsic quantum efficiency (IQE), or both the EQE and IQE of the specimen.

22. The system of claim 16, wherein the specimen measurement system comprises:
a reference detector configured to generate a first current of the plurality of currents, the first current being related to an intensity of the incident light signals; and
wherein a second current of the plurality of currents is generated by the specimen in response to the incident light signal.

23. The system of claim 16, wherein the specimen measurement system comprises:
a reference detector configured to generate a first current of the plurality of currents, the first current being related to an intensity of the incident light signals;
a reflectance detector configured to generate a second current of the plurality of currents, the second current being related to an intensity of a light signal reflected by the specimen in response to the incident light signals; and
wherein a third current of the plurality of currents is generated by the specimen in response to the incident light signals.

* * * * *